(12) United States Patent
Chory et al.

(10) Patent No.: US 6,768,043 B2
(45) Date of Patent: Jul. 27, 2004

(54) DAS5, A P450 PROTEIN INVOLVED IN THE BRASSINOSTEROID BIOSYNTHESIS PATHWAY IN PLANTS

(75) Inventors: Joanne Chory, Del Mar, CA (US); Zhiyong Wang, Palo Alto, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/995,917

(22) Filed: Nov. 27, 2001

(65) Prior Publication Data

US 2003/0150025 A1 Aug. 7, 2003

(51) Int. Cl.$^7$ .................. C12N 15/82; C12N 15/29; C12N 15/87; A01S 5/00
(52) U.S. Cl. .................. 800/290; 800/278; 800/287; 800/298; 536/23.1; 536/23.6; 435/468
(58) Field of Search ................ 800/290, 295, 800/298, 278, 287; 536/23.1, 23.6, 23.2; 435/410, 468, 419

(56) References Cited

U.S. PATENT DOCUMENTS

| | | | |
|---|---|---|---|
| 4,346,226 A | 8/1982 | Thompson et al. | 549/268 |
| 4,407,956 A | 10/1983 | Howell | 435/172 |
| 5,952,545 A | 9/1999 | Koncz et al. | 800/298 |

OTHER PUBLICATIONS

Bowie et al (1990, Science 247:1306–10).*
McConnell et al (2001, Nature 411 (6838):709–713).*
Finnegan and McElroy, 1994. Bio/technology 12:883–888.*
Eshed et al (2001, Current Biology 11:1251–1260.*
Zhao et al (2001, Science 291 :306–309).*
Beven et al (Apr., 2000, NCBI Accession No. AL163817.1).*
Adam, et al., *Phytochem.*, 25:1787 (1986).
Altschul, et al., *J. Mol. Biol.*, 215:403 (1990).
Altschul, et al., *Meth Enzymol.*, 266:460 (1996).
Altschul, et al., *Nature Genet.*, 6:119 (1994).
Altschul, et al., *Nucleic Acids Res.*, 25:3389 (1997).
Atanassova, et al., *Plant J.*, 2:291 (1992).
Bitter, et al., *Methods in Enymology*, 153:516 (1987).
Brisson, et al., *Nature*, 310:511 (1984).
Broglie, et al., *Science*, 224:838 (1984).
Choe, et al., *Plant Cell*, 10:231 (1998).
Coruzzi, et al., *Embo J.*, 3:1671 (1984).
Cutler et al., Brassinosteroids: chemistry, bioactivity, and applications, *ACS Symposium Series 474*, Washington DC: American Chemical Society (1991).
De Framond, *Biotechnology*, 1: 262 (1983).
Deng, et al., *Cell*, 76:423 (1994).
Devereux et al., *Nucl. Acids Res.*, 12:387 (1984).
Fromm, et al., *Proc. Natl. Acad. Sci., U.S.A.*, 82:5824 (1985).
Fujioka, et al., *Plant Cell Physiol.*, 37:1201 (1996).

Grove, et al., *Nature*, 281:216 (1979).
Gurley, et al., *Mol. Cell. Biol.*, 6:559 (1986).
Harlow and Lane, *Antibodies: A Laboratory Manual*, Cold Spring Harbor Laboratory,.
Hershey, et al., *Plant Mol. Biol.*, 17:679 (1991).
Hoekema, et al., *Nature*, 303:179 (1983).
Horsch, et al. *Science*, 227:1229 (1985).
Mansour Ioualalen, *C. R. Acad. Sci.* Paris, 316:1194 (1993).
Ito, et al., *Plant Mol. Biol.*, 24:863 (1994).
Jaye, et al., *Nucl. Acid Res.*, 11:2325 (1983).
Kauschmann, et al., *Plant Jour.*, 9:701 (1996).
Klee, et al., *Annu. Rev. Plant Physiol. Plant Mol. Biol.*, 42:529 (1991).
Klee, et al., *Annu. Rev. Plant Physiol.*, 38:467 (1987).
Klein, et al., *Nature*, 327:70, 1987.
Kohler, et al., *Nature*, 256:495, 1975, Laboratory, N.Y.
Li, et al., *Cell*, 90:929, 1997.
Madden, et al., *Meth. Enzymol.*, 266:131, 1996.
Mandava, et al., *Ann. Rev. Plant Physiol. Plant Mol. Biol.*, 39:23, 1988.
Maniatis et al., Molecular Cloning A Laboratory Manual, Cold Spring Harbor (1989).
Martinez, et al., *Proc. Natl. Acad. Sci., USA*, 89:7360, 1992.
Medford, et al., *Plant Cell*, 3:359, 1991;.
Mett, et al., *Proc. Natl. Acad. Sci., U.S.A.*, 90:4567, 1993, New York (1988).
Noguchi et al., *Plant Physiol.*, 121:743–752 (1999).
Odell, et al., *Nature*, 313:810 (1985).
Rogers et al., *Methods For Plant Mol. Biol.*, 423–463 (1988).
Schena, et al., *Proc. Natl. Acad. Sci., U.S.A.*, 88:10421, 1991, Section VIII, pp. 421–463.
Severin, et al., *Plant Mol. Biol.*, 15:827, 1990.
Szekeres, et al., *Cell*, 85:171, 1996.
Takamatsu, et al., *Embo J.*, 6:307, 1987.
Tatusova, et al., *Fems Microbiol Lett.*, 174:247, 1999.
Velten, et al., *Embo J.*, 3:2723, 1984.
Wallace, et al., *Nucl. Acid Res.*, 9:879, 1981.
Wang et al., *Nature*, 410:380, 2001.
Weigel, et al. *Plant Physiol.* 122:1003, 2000.
Wissenbach, et al., *Plant Journal*, 4:411, 1993.
Xu, et al., *Plant Cell*, 7:1555, 1995.
Zurek, et al., *Plant Physiol.*, 104:505, 1994.

\* cited by examiner

*Primary Examiner*—Phuong T. Bui
*Assistant Examiner*—Stuart F. Baum
(74) *Attorney, Agent, or Firm*—Morrison & Foerster LLP

(57) ABSTRACT

The present invention provides a cytochrome P450-encoding gene, DAS5, as well as an altered gene, das5-D, which are involved in the synthesis of the plant steroid hormone brassinolide. The das5-D mutant has an insertion of a T-DNA containing transcriptional enhancers into its promoter region. Overexpression of the mutant thus produces large amounts of DAS5 transcript. The expression of this das5-D mutation or overexpression of the DAS5 gene in transgenic plants causes such plants to become significantly larger and more robust than their wild-type counterparts, thus increasing plant yields.

18 Claims, No Drawings

DAS5, A P450 PROTEIN INVOLVED IN THE BRASSINOSTEROID BIOSYNTHESIS PATHWAY IN PLANTS

GOVERNMENT RIGHTS

This invention was made with government support under U. S. Department of Agriculture (USDA) grant #99-35301-7903. The government may have certain rights in the invention.

BACKGROUND OF THE INVENTION

1. Field of the Invention

The present invention relates to the field of plant biology and specifically to methods of modifying brassinosteroid levels in plants by altering levels of a specific cytochrome P450 protein involved in the brassinosteroid biosynthesis pathway. Genetic modifications of plants to increase the expression of DAS5 results in a variety of useful phenotypes such as increased fresh weight and increased overall plant size.

2. Description of the Related Art

Plant growth is coordinated by both external stimuli and internal mechanisms leading to changes in both cell division and cell expansion. In Arabidopsis, cell elongation is largely responsible for hypocotyl growth in germinating seedlings and the bolting of inflorescences at the end of vegetative growth. The main external signal is light (Deng, et al., *Cell* 76:423, 1994), which inhibits hypocotyl elongation and promotes cotyledon expansion and leaf development. The internal signaling mechanisms are generally regulated by plant growth substances (Klee, et al., *Annu. Rev. Plant Physiol. Plant Mol. Biol.* 42:529 1991). One class of these plant growth substances is the brassinosteroids.

Brassinosteroids produce a variety of phenotypic responses. For example, brassinosteroids accelerate seed germination and growth of seedlings, increase cell size and elongation, alter the arrangement of cortical microtubules and cellulose microfilaments, promote differentiation of xylem, promote leaf enlargement, increase plant dry weight, induce H+ export and membrane hyperpolarization, promote tissue senescence in the dark, repress anthocyanin production in light-grown plants, and induce plant pathogen resistance responses to numerous bacterial and fungal species.

Plants with altered brassinosteroid levels may be of particular economic importance to agriculture. Brassinosteroids may increase plant growth rates or alter the reproductive cycle of plants. Modification of brassinosteroid pathways may produce plants with higher crop yields and improved stress resistance (Cutler et al., *Brassinosteroids: chemistry, bioactivity, and applications*. ACS Symposium Series 474. Washington D.C.: American Chemical Society, 1991). Additionally, brassinosteroids may protect plants from insect attack, and qualify for classification as biochemical pesticides.

Brassinolide, one of the major brassinosteroids, was first isolated from the pollen of rape (*Brassica napus*) (Grove, et al., *Nature,* 281:216 1979), and was found to be a novel plant growth-promoting factor. To date, about 40 brassinosteroids have been found. Brassinosteroids are present at very low concentrations, and have been found to occur in all plant species examined (for review, see Mandava, et al., *Ann. Rev. Plant Physiol. Plant Mol. Biol.* 39:23, 1988).

Several methods for the chemical synthesis of brassinosteroids have been described. For example, U.S. Pat. No. 4,346,226 to Thompson discloses a method for producing synthetic polyhydroxylated steroidal lactones for use as plant growth promoting substances. Other methods are reviewed in Adam, et al., *Phytochem.* 25:1787, 1986). Historically, commercial use of the brassinosteroids for agricultural applications has been limited due to the difficulty and expense involved in producing them. In field trials, plants were found to have poor uptake of steroids through the plant epidermis, and the resulting amount of steroids required for application was considerable. Furthermore, due to the high cost of brassinolide treatments, the exogenous application of brassinosteroid compounds to increase agricultural characteristics has not been agronomically useful.

Both mutational and biochemical analyses have been beneficial in elucidating the brassinosteroid biosynthetic pathway. Several mutations have been identified that affect either light-dependent or hormone signaling pathways, resulting in plants with a dwarf phenotype. At least some of these dwarf mutants have been found to be defective in aspects of brassinosteroid biosynthesis, since they can be rescued by brassinosteroid application.

Brassinosteroids are synthesized via multiple parallel pathways (Fujioka, et al., *Plant Cell Physiol.* 37:1201, 1996). A multistep biosynthetic pathway leads from the sterol precursor cycloartenol to brassinolide, which is the most active of the many brassinosteroid compounds. Common plant sterols include sitosterol, stigmasterol, campesterol, 24-epicampesterol, and cholesterol are derived from cycloartenol. Most of these compounds may function as brassinosteroid precursors. A multistep pathway leads from the sterol cycloartenol to the sterol campesterol. The Arabidopsis dwf7 mutant blocks biosynthesis of 5-dehydroepisterol from episterol, while the mutant dwf5 blocks 24-methylenecholesterol biosynthesis from 5-dehydroepisterol. The mutants dim, dwf1, and 1 kb block synthesis of campesterol from 24-methylenecholesterol.

The synthesis of 5 α-campestanol from campesterol is blocked in the det2 mutant of Arabidopsis. The DET2 gene encodes a steroid 5 α-reductase. Overexpression of the DET2 protein increases brassinolide levels and results in larger, more robust plants. The pathway from campesterol to deoxycathasterone (or, alternatively, from 6-oxocampestanol to cathasterone) is blocked in the dwf4 mutant. The DWF4 gene and corresponding protein have been described in WO0047715 to Azpiroz. The next biosynthetic steps for each of these compounds is blocked in the mutant cpd (disclosed in U.S. Pat. No. 5,952,545 to Koncz). Both the CPD protein and DWF4 protein are types of cytochrome P450 proteins.

Once brassinolide is synthesized, it must be perceived by some cellular moiety, and then transduced to regulate developmental processes. Mutants in brassinosteroid perception are also of utility to study this aspect of brassinolide pathways. For example, three brassinosteroid insensitive mutants bri1, lka, and cu-3 accumulate brassinosteroids and impair brassinosteroid signaling. A brassinosteroid up regulated gene (BRU1) (Zurek, et al., *Plant Physiol* 104:505, 1994) was found to be a xyloglucan endotransglycosylase (XET), which may be involved in cell wall loosening during elongation. Brassinosteroid regulates the TCH4 gene, which is also an XET (Xu, et al., *Plant Cell* 7:1555, 1995).

The brassinosteroid insensitive mutant, as well as its allelic mutant cbb2 (Kauschmann, et al., *Plant Jour.* 9:701, 1996) were found to belong to the leucine-rich-repeat receptor-like kinase family of proteins (Li, et al., *Cell* 90:929, 1997). The BRI1 polypeptide is the brassinosteroid receptor (Wang et al., *Nature,* 410:380, 2001).

SUMMARY OF THE INVENTION

In one embodiment of the invention a method of producing a genetically modified plant having increased size as compared to a wild-type plant is produced by contacting a plant cell with at least one nucleic acid sequence encoding a DAS5 protein, wherein the nucleic acid sequence is operably associated with a promoter, to obtain a transformed plant cell, then producing a plant from the transformed plant cell, and finally selecting a plant exhibiting increased size.

Another embodiment of the present invention provides a genetically modified plant exhibiting increased size in comparison to a wild-type plant, wherein the genetically modified plant includes at least one exogenous nucleic acid sequence encoding a DAS5 polypeptide, wherein the amino acid sequence of the polypeptide is at least 80% homologous to SEQ ID NO: 1.

Yet another embodiment of the present invention provides a genetically modified seed which produces a plant exhibiting increased size in comparison to a wild-type plant, wherein the genetically modified seed includes at least one exogenous nucleic acid sequence encoding a DAS5 polypeptide with an amino acid sequence of at least 80% sequence homology to SEQ ID NO: 1.

In another embodiment of the present invention, a substantially purified DAS5 polypeptide having cytochrome P450 activity and functioning in the brassinolide biosynthetic pathway is provided.

In a further embodiment of the present invention, an antibody which binds to an isolated DAS5 polypeptide or antigenic fragments thereof is provided.

In yet another embodiment of the invention, an isolated DAS5 polynucleotide encoding the amino acid sequence of SEQ ID NO: 1 is provided.

DETAILED DESCRIPTION OF THE PREFERRED EMBODIMENT

The present disclosure provides identification of nucleic acid molecules encoding proteins involved in the synthesis of brassinosteroids in plants, methods of increasing endogenous levels of brassinosteroid levels in plants, insect protection, and methods of increasing plant biomass by modulating levels of brassinosteroid pathway components. Without wishing to be limited to a particular theory, these molecules appear to modulate brassinosteroid response pathways at the level of their biosynthetic enzymes, therefore altering brassinosteriod-related responses and signaling pathways.

An altered gene, DAS5, is disclosed which is involved in the synthesis of brassinolides. The das5-D mutant was formed by insertional mutagenesis and activation tagging procedure, wherein a T-DNA containing a transcriptional enhancer were randomly inserted into Arabidopsis genomes. The mutant gene resulting from activation tagging acts like a dominant mutation, as activation tagging results in increased expression of the protein which has been "tagged". It was observed that one of the plants obtained from an activation tagging mutagenesis procedure was larger than control plants. Upon further analysis, it was found that this larger plant contained an activation tagged mutation upstream of the DAS5 gene sequence. This produced the das5-D mutant phenotype wherein the DAS5 protein is produced at high levels, resulting in a larger plant phenotype.

The DAS5 gene encodes a member of the P450 family of proteins. P450 proteins are membrane-associated NAD(P) H-dependent monooxygenases which normally form a complex with reductases. Cytochrome P450 proteins typically have characteristic conserved domains including the N-terminal membrane-anchoring domain, the proline rich domain, the heme-binding domain and the oxygen-binding domain. Several P450 proteins exist in plants, where some cytochrome P450 proteins have been found to specifically hydroxylate plant steroid compounds at certain steps in the brassinolide synthesis pathway. For example, the DWF4 is a cytochrome P450 protein involved in the hydroxylation step from 5 α-campestanol to 6-deoxocathasterone, or, in an alternative pathway, the step from 6-oxocampestanol to cathasterone. The CONSTITUTIVE PHOTOMORPHOGENESIS AND DWARFISM protein (CPD) is a cytochrome P450 protein thought to be involved in the formation of 6-deoxoteasterone from 6-deoxycathasterone or, alternatively, the formation of teasterone from cathasterone.

The das5-D mutant was generated using an activation tagging approach of Weigel, et al. (*Plant Physiol.* 122:1003, 2000), the entire disclosure of which is hereby incorporated by reference. Briefly, T-DNA vectors containing multimers of transcriptional enhancers from the cauliflower mosaic virus 35S were combined with a marker gene to create a vast number of mutant plants. Plants were transformed using a modified vacuum-infiltration method (Bechtold, et al., *Methods Mol. Biol.* 82: 259, 1998). The resulting mutant plants were selected for the presence of resistance to the herbicide glufosinate (Basta). Since this method yields dominant phenotypes that are apparent in the hemizygous state, the transformed plants could be screened directly for mutant phenotypes.

The activation tagging procedure often produces dominant mutations, whereby the gene product of the altered gene is produced at high levels. This is in contrast to many mutational methods that tend to create gene products that are either nonfunctional or poorly functional. Accordingly, the activation tag present in the upstream regulatory region of the DAS5 gene triggers its increased expression, leading to the das5-D mutant phenotype. By "das5-D" is meant the DAS5 gene additionally containing upstream activation sequences which cause a high level of DAS5 transcript and, consequently, high levels of DAS5 protein production in cells containing this construct. Therefore, the das5-D is a dominant acting mutation, in contrast to types of mutations that inactivate protein function.

Accordingly, though das5-D may be termed a "mutation" giving rise to a mutant phenotype, transgenic plants carrying this altered gene are expected to have high levels of DAS5 gene expression and high levels of active DAS5 protein as compared to wild type plants. Both overexpression of the DAS5 gene and expression of the dominant activation-tagged das5-D mutation of this invention resulted in increased brassinosteroid levels throughout the plant and produce the das5-D mutant phenotype. For example, when das5-D was expressed in wild type plants, the fresh weight increased by approximately 26%. It is expected that the increase in brassinosteroid levels and plant biomass produced in response to an increase in DAS5 gene expression may increase disease resistance, thermotolerance, and general stress protection. The phenotype of plants with decreased DAS5 gene expression are identical to the phenotype of control plants.

DAS5 Polypeptides

In one embodiment, the present invention provides a substantially pure DAS5 polypeptide having the amino acid sequence shown in SEQ ID NO: 1. The DAS5 polypeptide is characterized by having cytochrome P450 activity and functioning in the brassinolide biosynthetic pathway.

The term "substantially pure" as used herein refers to DAS5 polypeptide which is substantially free of other proteins, lipids, carbohydrates or other materials with which it is naturally associated. One skilled in the art can purify DAS5 using standard techniques for protein purification. The purity of the DAS5 polypeptide can also be determined by amino-terminal amino acid sequence analysis.

Embodiments of the invention also include functional DAS5 polypeptides, and functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of DAS5 polypeptide", refers to all fragments of DAS5 that retain DAS5 activity including, but not limited to, having cytochrome P450 activity functioning in the brassinolide biosynthetic pathway or being recognized by antibodies or probes directed to DAS5 proteins. Biologically functional fragments, for example, can vary in size from a polypeptide fragment as small as an epitope capable of binding an antibody molecule to a large polypeptide capable of participating in the characteristic induction or programming of phenotypic changes within a cell.

The P450 activity of DAS5 and the role of DAS5 in the brassinolide biosynthetic pathway can be utilized in bioassays to identify biologically active fragments, mutants, and variants of DAS5 polypeptide and related polypeptides. Assays can be performed to detect the enzymatic activity of DAS5.

Minor modifications of the DAS5 primary amino acid sequence may result in proteins which have substantially equivalent activity to the DAS5 polypeptide described herein in SEQ ID NO: 1. Such modifications may be deliberate, as for example by site-directed mutagenesis, or may be spontaneous. Modified polypeptides produced by these modifications having the biological activity of DAS5 is present such as cytochrome P450 activity, increased plant biomass, and increased crop yield, are included herein. As used herein, the term "yield" or "plant yield" refers to increased plant growth, increased crop growth, and/or increased biomass production. Further, deletion of one or more amino acids can also result in a modification of the structure of the resultant molecule without significantly altering its activity. This can lead to the development of a smaller active molecule which could have broader utility.

DAS5 polypeptide includes amino acid sequences substantially the same as the sequence set forth in SEQ ID NO: 1. The term "substantially the same" refers to amino acid sequences that retain the activity of DAS5 as described herein, including but not limited to cytochrome P450 activity and function in the brassinolide biosynthetic pathway. DAS5 polypeptides of the invention include conservative variations of the polypeptide sequence that produce sequences that are substantially the same as the sequence set forth in SEQ ID NO: 1. The term "conservative variation" as used herein denotes the replacement of an amino acid by another biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Proteins of the invention can be analyzed by standard methods of analysis including, but not limited to, immunoprecipitation, SDS-PAGE, immunoblotting, and chromatography. In addition, the in vitro synthesized (IVS) protein assay as described in the present examples can be used to analyze DAS5 protein product.

Another aspect of the invention includes polypeptides or fragments thereof having at least about 70%, at least about 80%, at least about 85%, at least about 90%, at least about 95%, or more than about 95% homology to one of the polypeptides of SEQ ID NO: 1, and sequences substantially identical thereto, or a fragment comprising at least 5, 10, 15, 20, 25, 30, 35, 40, 50, 75, 100, 150, 200, 250, 300, or 350 consecutive amino acids thereof. Homology may be determined using any of the methods described herein which align the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of SEQ ID NO: 1, and sequences substantially identical thereto, or a fragment comprising at least about 5, 10, 15, 20, 25, 30, 35, 40, 50, 75, 100, 150, 200, 250, 300, or 350 consecutive amino acids thereof may be obtained by isolating the nucleic acids encoding them using the techniques described herein Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NO: 1, and sequences substantially identical thereto, or a fragment comprising at least about 5, 10, 15, 20, 25, 30, 35, 40, 50, 75, 100, 150, 200, 250, 300, or 350 consecutive amino acids thereof using any of the programs described above.

Homologous amino acid or nucleotide sequences of the present invention preferably comprise enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool) (for a review see Altschul, et al., *Meth Enzymol.* 266:460, 1996; and Altschul, et al., *Nature Genet.* 6:119, 1994). BLAST is the heuristic search algorithm employed by the programs blastp, blastn, blastx, tblastn, and tblastx using the statistical methods of Karlin and Altschul (available at www.ncbi.nih.gov/BLAST) Altschul, et al., *J. Mol. Biol.* 215:403, 1990). The BLAST programs were tailored for sequence similarity searching, for example to identify homologues to a query sequence. The BLAST pages offer several different databases for searching. Some of these databases, such as *ecoli*, dbEST and month, are subsets of the NCBI (National Center for Biotechnology Information) databases, while others, such as SwissProt, PDB and Kabat are compiled from outside sources. Protein BLAST allows one to input protein sequences and compare these against other protein sequences.

The five BLAST programs available at Internet website:www.ncbi.nlm.nih.gov perform the following tasks:

blastp—compares an amino acid query sequence against a protein sequence database.

blastn—compares a nucleotide query sequence against a nucleotide sequence database.

blastx—compares the six-frame conceptual translation products of a nucleotide query sequence (both strands) against a protein sequence database.

tblastn—compares a protein query sequence against a nucleotide sequence database dynamically translated in all six reading frames (both strands).

tblastx—compares the six-frame translations of a nucleotide query sequence against the six-frame translations of a nucleotide sequence database.

Other computer program methods to determine identity and similarity between the two sequences include but are not limited to the GCG program package (Devereux, et al., *Nucl. Acids Res.* 12:387, 1984) and FASTA (Atschul, et al., *J. Molec. Biol.* 215:403, 1990). By "percentage identity" is meant % of identical amino acids between the two compared proteins. By "% similarity" is meant the percentage of similar amino acids between the two compared proteins.

A BLAST search was performed using the DAS5 polypeptide sequence (SEQ ID NO: 1) as a query. Several accessions containing sequences of cytochrome P450 proteins were found as follows:

gi/11357546: "hypothetical protein F18022.190" from *Arabidopsis thaliana*. Pairwise comparison with DAS5: 99% identity (380/382 amino acids), 99% similarity (381/382).

gi/5915851 (GenBank Accession #Q42569), a cytochrome P450 from *Arabidopsis thaliana* (Szekeres, et al., Cell 85:171, 1996). Pairwise comparison with DAS5: 34% identity (149/409), 50% similarity (210/409).

gi/2935342 (GenBank Accession #AF044216), DWF4, a cytochrome P450 from *Arabidopsis thaliana* (Choe, et al., *Plant Cell* 10:231, 1998): 34% identity (160/465), 52% similarity (247/465).

gi/9587211 (Accession #AAF89209), a cytochrome P450 isolated from *Vigna radiata;* 33% identity (140/421), 50% similarity (212/421).

gi/13878393 (Accession #Q9MO66), a cytochrome P450 (ROTUNDIFOLIA3) isolated from Arabidopsis; 32% identity (141/438), 49% similarity (216/438).

gi/14209594 (Accession #BAB56089), a cytochrome P450 isolated from *Oryza sativa;* 30% identity (131/431), 50% similarity (218/431).

Screening for Molecules that interact or Bind with DAS5

Other embodiments of the present invention provide methods of screening or identifying proteins, small molecules or other compounds which are capable of inducing or inhibiting the expression of the DAS5 genes and proteins. The assays may be performed in vitro using transformed or non-transformed cells, immortalized cell lines, or in vivo using transformed plant models enabled herein. In particular, the assays may detect the presence of increased or decreased expression of DAS5 genes or DAS5 proteins on the basis of increased or decreased mRNA expression, increased or decreased levels of DAS5 protein products, or increased or decreased levels of expression of a marker gene (e.g., beta-galactosidase, green fluorescent protein, alkaline phosphatase or luciferase) operably joined to a DAS5' regulatory region in a recombinant construct. Cells known to express a particular DAS5 polypeptide, or transformed to express a particular DAS5 polypeptide, are incubated and one or more test compounds are added to the medium. After allowing a sufficient period of time, e.g., anywhere from 0–72 hours, or longer, for the compound to induce or inhibit the expression of the DAS5, any change in levels of expression from an established baseline may be detected using any of the techniques described above.

Additional embodiments of the present invention provide methods for identifying proteins and other compounds which bind to, or otherwise directly interact with, the DAS5 protein. The proteins and compounds will include endogenous cellular components which interact with DAS5 in vivo and which, therefore, provide new targets for agricultural products, as well as recombinant, synthetic and otherwise exogenous compounds which may have DAS5 binding capacity and, therefore, may be candidates for plant growth modulators. Thus, in one series of embodiments, high throughput screen (HTS) protein or DNA chips, cell lysates or tissue homogenates may be screened for proteins or other compounds which bind to one of the normal or mutant DAS5 genes. Alternatively, any of a variety of exogenous compounds, both naturally occurring and/or synthetic (e.g., libraries of small molecules or peptides), may be screened for DAS5 binding capacity.

In various embodiments, an assay is conducted to detect binding of DAS5 and another moiety. The DAS5 in these assays may be any polypeptide comprising or derived from a normal or mutant DAS5 protein, including functional domains or antigenic determinants of the DAS5 fusion proteins. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of DAS5 components and bound proteins or other compounds by immunoprecipitation; (3) BIAcore analysis; and (4) yeast two-hybrid systems.

Additional embodiments of the present invention provide methods of identifying proteins, small molecules and other compounds capable of modulating the activity of normal or mutant DAS5.

Additional embodiments of the present invention provide methods of identifying compounds on the basis of their ability to affect the expression of DAS5, the activity of DAS5, the activity of other DAS5-regulated genes, the activity of proteins that interact with normal or mutant DAS5 proteins, the intracellular localization of DAS5, changes in transcription activity, the presence or levels of DAS5, or other biochemical, histological, or physiological markers which distinguish cells bearing normal and modulated DAS5 activity in plants and in animals. Methods of identifying compounds with activity toward the DAS5 gene or the DAS5 protein may be practiced using normal cells or plants, the transformed cells and plant models of the present invention, or cells obtained from subjects bearing normal or mutant DAS5 genes.

In accordance with another aspect of the invention, the proteins of the invention can be used as starting points for rational chemical design to provide ligands or other types of small chemical molecules. Alternatively, small molecules or other compounds identified by the above-described screening assays may serve as "lead compounds" in design of modulators brassinosteroid pathways in plants.

DAS5 Polynucleotides

Another embodiment provides a genomic DAS5 sequence having SEQ ID NO: 2. Embodiments of the invention also provide any isolated polynucleotide sequence encoding a polypeptide having the amino acid sequence of SEQ ID NO: 1. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode DAS5. It is understood that polynucleotides encoding all or varying portions of DAS5 are included herein, as long as they encode a polypeptide with DAS5 activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription. As used herein, the terms "polynucleotides" and "nucleic acid sequences" refer to DNA, RNA and cDNA sequences.

Embodiments of the present invention provide the complete DAS5 cDNA sequence (SEQ ID NO: 3), encoding the DAS5 protein (SEQ ID NO: 1). Also included in embodiments of the invention are nucleotide sequences that are greater than 70% homologous with the sequence of SEQ ID NO: 3, but still retain the ability to modulate brassinosteroid levels in plants. Other embodiments of the invention include nucleotide sequences that are greater than 75%, 80%, 85%, 90% or 95% homologous with the sequence of SEQ ID NO: 3, but still retain the ability to modulate brassinosteroid levels in plants.

DAS5 polynucleotides of the present invention include polynucleotides having alterations in the nucleic acid sequence, where such polynucleotides still encode a polypeptide having the ability to modulate brassinosteroid levels. Alterations in DAS5 nucleic acids within the scope of the present invention include, but are not limited to, intragenic mutations such as point mutations, nonsense (stop) mutations, antisense, splice site and frameshift mutations, as well as heterozygous or homozygous deletions. Such alterations may be detected by standard methods known to those of skill in the art including sequence analysis, Southern blot analysis, PCR based analyses (e.g., multiplex PCR, sequence tagged sites (STSs)) and in situ hybridization. Embodiments of the invention also include anti-sense polynucleotide sequences, where an antisense sequence may be complementary to the entire sequence, or any fragment thereof.

The polynucleotides described herein include sequences that are degenerate as a result of the genetic code. There are 20 natural amino acids, most of which are specified by more than one codon. Therefore, all degenerate nucleotide sequences are included in the invention as long as the DAS5 polypeptide encoded by such nucleotide sequences retains DAS5 activity. A "functional polynucleotide" denotes a polynucleotide which encodes a functional polypeptide as described herein. Embodiments of the invention include polynucleotides encoding a polypeptide having the biological activity of the polypeptides having the amino acid sequence of SEQ ID NO: 1 and having at least one epitope for an antibody immunoreactive with DAS5 polypeptide.

In one embodiment, the polynucleotides encoding DAS5 include the nucleotide sequence SEQ ID NO: 3 and nucleic acid sequences complementary thereto. A complementary sequence may include an antisense nucleotide. When the sequence is RNA, the deoxyribonucleotides A, G, C, and T of SEQ ID NO: 3 are replaced by ribonucleotides A, G, C, and U, respectively. Embodiments of the invention include fragments or "probes" of the above-described nucleic acid sequences, wherein the fragments or probes are at least 15 bases in length, which is presumed to be sufficient to permit the probe to selectively hybridize to DNA encoding the protein of SEQ ID NO: 1.

Polynucleotide sequences of the invention may be obtained by several methods. For example, the polynucleotide can be isolated using hybridization or computer-based techniques which are well known in the art including, but not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

"Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated DAS5 nucleotide sequences.

Screening procedures which rely on nucleic acid hybridization make it possible to isolate any gene sequence from any organism, provided the appropriate probe is available. Oligonucleotide probes corresponding to any part of a nucleotide sequence encoding a protein having DAS5 activity can be synthesized chemically. This requires that short, oligopeptide stretches of the amino acid sequence must be known. The DNA sequence encoding the protein can be deduced from the genetic code, and the degeneracy of the code must be taken into account. When the sequence is degenerate, it is possible to perform a mixed addition reaction, which includes a heterogeneous mixture of denatured double-stranded DNA. For screening procedures, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. By using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981). Alternatively, a subtractive library, as illustrated herein is useful for elimination of non-specific cDNA clones.

Among the standard procedures for isolating cDNA sequences of interest is the formation of plasmid- or phage-carrying cDNA libraries which are derived from reverse transcription of mRNA from donor cells that have a high level of genetic expression. When used in combination with polymerase chain reaction technology, even low-abundance expression products can be cloned. In those cases where significant portions of the amino acid sequence of the polypeptide are known, the production of labeled single or double-stranded DNA or RNA probe sequences duplicating a sequence putatively present in the target cDNA may be employed in hybridization procedures carried out on copies of the cDNA which have been denatured to give single-stranded molecules (Jay, et al., Nucl. Acid Res., 11:2325, 1983).

Antibodies

The invention also provides antibodies immunoreactive with any DAS5 polypeptide, or antigenic fragments thereof, where an antibody may consist essentially of pooled monoclonal antibodies with different epitopic specificities, as well as distinct monoclonal antibody preparations is provided. Monoclonal antibodies are made from antigen containing fragments of the protein by methods well known to those skilled in the art (Kohler, et al., Nature, 256:495, 1975).

The term "antibody" as used in this invention includes intact molecules as well as fragments thereof, such as Fab, F(ab')2, and Fv capable of binding to an epitopic determinant present in DAS5 polypeptide. Such antibody fragments retain some ability to selectively bind with its antigen or receptor.

Methods of making these fragments are known in the art. (See for example, Harlow and Lane, Antibodies: A Laboratory Manual, Cold Spring Harbor Laboratory, New York (1988), incorporated herein by reference).

As used in this invention, the term "epitope" refers to an antigenic determinant on an antigen to which the paratope of an antibody binds. Epitopic determinants often consist of chemically active surface groupings of molecules such as amino acids or sugar side chains and usually have specific three dimensional structural characteristics, as well as specific charge characteristics.

Antibodies which bind to the DAS5 polypeptide of the invention can be prepared using an intact polypeptide or fragments containing small peptides of interest as the immunizing antigen. For example, it may be desirable to produce antibodies that specifically bind to the N- or C-terminal domains of DAS5. The polypeptide or peptide used to immunize an animal may be derived from translated cDNA or may be chemically synthesized, and may further be conjugated to a carrier protein, if desired. Commonly used carriers which are chemically coupled to an immunizing peptide include keyhole limpet hemocyanin (KLH), thyroglobulin, bovine serum albumin (BSA), and tetanus toxoid.

Polyclonal or monoclonal antibodies can be further purified, for example, by binding to and eluting from a matrix to which the polypeptide or a peptide to which the antibodies were raised is bound. Those of skill in the art are familiar with various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

A cDNA expression library such as lambda gt11, can be screened indirectly for DAS5 peptides using antibodies specific for DAS5 epitopes. Such antibodies may be polyclonally or monoclonally derived, and may be used to detect expression product indicative of the presence of DAS5 cDNA.

Vectors

DAS5 polynucleotide sequences of the present invention can be expressed in vitro by transfer of DAS5 sequences into a suitable host cell. "Host cells" are cells in which a vector containing a coding region can be propagated and its DNA expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

The DAS5 polynucleotide sequences according to the present invention may be inserted into a recombinant expression vector. The terms "recombinant expression vector" or "expression vector" refer to a plasmid, virus or other vehicle known in the art that has been manipulated by insertion or incorporation of the DAS5 genetic sequence. Such expression vectors contain a promoter sequence which facilitates the efficient transcription of the inserted DAS5 sequence. The expression vector typically contains an origin of replication, a promoter, and one or more genes that allow phenotypic selection of the transformed cells.

Methods well known to those skilled in the art can be used to construct expression vectors containing the DAS5 coding sequence and appropriate transcriptional/translational control signals. These methods include in vitro recombinant DNA techniques, synthetic techniques, and in vivo recombination/genetic techniques.

A variety of host-expression vector systems may be utilized to express the DAS5 coding sequence in numerous types of organisms. These include, but are not limited to, microorganisms such as bacteria transformed with recombinant bacteriophage DNA, plasmid DNA or cosmid DNA expression vectors containing the DAS5 coding sequence; yeast transformed with recombinant yeast expression vectors containing the DAS5 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the DAS5 coding sequence; insect cell systems infected with recombinant virus expression vectors (e.g., baculovirus) containing the DAS5 coding sequence; or animal cell systems infected with recombinant virus expression vectors (e.g., retroviruses, adenovirus, vaccinia virus) containing the DAS5 coding sequence, or transformed animal cell systems engineered for stable expression.

Any of a number of suitable transcription and translation elements, including constitutive and inducible promoters, transcription enhancer elements, and/or transcription terminators, may be used in the expression vector (see e.g., Bitter, et al., Methods in Enzymology 153:516, 1987). The choice of these elements will vary depending on the host/vector system utilized. The particular promoter selected should be capable of causing sufficient expression to result in the production of an effective amount of DAS5 gene product. The promoters used in the vector constructs of the present invention may be modified, if desired, to affect their control characteristics.

For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted DAS5 coding sequence.

As an additional example, vectors for gene expression in plants may contain any of a number of promoters that are functional in plants. Many types of plant-derived promoters as well promoters derived from other sources that are functional in plants are now known. Some types of plant-derived promoters may be constantly active. Others may be active only in certain circumstances or cell types. Examples of this later group include tissue-specific, developmentally specific, stress-specific, or environmentally specific promoters. Additionally, developmental, tissue-specific, and environmentally inducible promoters may be combined at the upstream regulatory region of a DAS5 gene sequence to carefully regulate the spacial and temporal production of DAS5 polypeptide in order to produce novel, desirable plant phenotypes.

Isolation and purification of recombinantly expressed polypeptide, or fragments thereof, provided by the invention, may be carried out by conventional means including chromatographic and immunological separations involving monoclonal or polyclonal antibodies.

Gene Transfer to Plants

The term "genetic modification" as used herein refers to the introduction of one or more heterologous nucleic acid sequences, e.g., a DAS5-encoding sequence, into one or more plant cells which can then be used to generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete-producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or Brassica oleracea (e.g., cabbage, broccoli, cauliflower, brussel sprouts), radish, carrot, beets, eggplant, spinach, cucumber, squash, melons, cantaloupe, sunflowers and various ornamentals. Examples of woody species include poplar, pine, sequoia, cedar, oak, fir, hemlock, ash, cherry, etc.

The term "heterologous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In the broad method of the invention, at least one nucleic acid sequence encoding DAS5 is operably linked with a promoter. It may be desirable to introduce more than one copy of DAS5 polynucleotide into a plant for enhanced DAS5 expression. For example, multiple copies of the gene would have the effect of increasing DAS5 expression and/or production of DAS5 polypeptides in the plant.

It may also be desirable to decrease levels of DAS5 expression in the plant. Any method to downregulate DAS5 gene expression may be used, but typical examples include antisense technology, cosuppression, RNA inhibition (RNAi), and ribozyme inhibition. In the antisense method, for example, antisense molecules are introduced into cells that contain DAS5, for example, and may function by decreasing the amount of DAS5 polypeptide production in a cell, or may function by a different mechanism. Antisense polynucleotides useful for the present invention are complementary to specific regions of a corresponding target mRNA. An antisense polynucleotide can be introduced to a cell by introducing an expressible construct containing a nucleic acid segment that codes for the polynucleotide. Antisense polynucleotides in context of the present invention may include short sequences of nucleic acid known as oligonucleotides, usually 10–50 bases in length, as well as longer sequences of nucleic acid that may exceed the length of the DAS5 gene sequence itself.

Genetically modified plants of the present invention are produced by contacting a plant cell with a vector including at least one nucleic acid sequence encoding DAS5. To be effective once introduced into plant cells, the DAS5 nucleic acid sequence must be operably associated with a promoter which is effective in the plant cells to cause transcription of DAS5. Additionally, a polyadenylation sequence or transcription control sequence recognized in plant cells may be employed. It is preferred that the vector harboring the nucleic acid sequence to be inserted also contain one or more selectable marker genes so that the transformed cells can be selected from non-transformed cells in culture, as described herein.

The term "operably associated" refers to functional linkage between a promoter sequence and the DAS5 nucleic acid sequence regulated by the promoter. The operably linked promoter controls the expression of the DAS5 nucleic acid sequence.

The expression of structural genes employed in the present invention may be driven by a number of promoters. The endogenous, or native promoter of a structural gene of interest may be utilized for transcriptional regulation of the gene, or the promoter may be a foreign regulatory sequence.

For plant expression vectors, suitable viral promoters include the 35S RNA and 19S RNA promoters of CaMV (Brisson, et al., *Nature,* 310:511, 1984; Odell, et al., *Nature,* 313:810, 1985); the full-length transcript promoter from Figwort Mosaic Virus (FMV) (Gowda, et al., *J. Cell Biochem.,* 13D: 301, 1989) and the coat protein promoter to TMV (Takamatsu, et al., *EMBO J.* 6:307, 1987). Alternatively, plant promoters such as the light-inducible promoter from the small subunit of ribulose bis-phosphate carboxylase (ssRUBISCO) (Coruzzi, et al., *EMBO J.,* 3:1671, 1984; Broglie, et al., *Science,* 224:838, 1984); mannopine synthase promoter (Velten, et al., *EMBO J.,* 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley, et al., *Mol. Cell. Biol.,* 6:559, 1986; Severin, et al., *Plant Mol. Biol.,* 15:827, 1990) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., *Proc. Natl. Acad. Sci., U.S.A.,* 90:4567, 1993); In2-1 and In2-2 regulator sequences which are activated by substituted benzenesulfonamides, e.g., herbicide safeners (Hershey, et al., *Plant Mol. Biol.,* 17:679, 1991); and the GRE regulatory sequences which are induced by glucocorticoids (Schena, et al., *Proc. Natl. Acad. Sci., U.S.A.,* 88:10421, 1991). Other promoters, both constitutive and inducible will be known to those of skill in the art.

The particular promoter selected should be capable of causing sufficient expression to result in the production of an effective amount of structural gene product, e.g., DAS5, to cause increased yield and/or increased biomass. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova, et al., *Plant J.,* 2:291, 1992). Other tissue specific promoters useful in transgenic plants, including the cdc2a promoter and cyc07 promoter, will be known to those of skill in the art. (See for example, Ito, et al., *Plant Mol. Biol.,* 24:863, 1994; Martinez, et al., *Proc. Natl. Acad. Sci. USA,* 89:7360, 1992; Medford, et al., *Plant Cell,* 3:359, 1991; Terada, et al., *Plant Journal.,* 3:241, 1993; Wissenbach, et al., *Plant Journal,* 4:411, 1993).

The upstream regions that control expression of the DAS5 gene may contain more than one promoter, and may additionally contain one or more enhancer elements. Such regions may be present, for example, in activation-tagging vectors (Weigel, et al., *Plant Physiol.* 122:1003, 2000), which contain multimerized transcriptional enhancers from the cauliflower mosaic virus (CaMV) 35S gene. In this method, the activation tagging sequence serves to upregulate endogenous genes that are downstream of the insertion site.

In one embodiment of this invention, the expression of the dominant DAS5 gene sequence may be controlled by the presence of an upstream "activation sequence", which contains one or more promoters (such as the 35S promoter derived from the cauliflower mosaic virus), plus multimers of 35S enhancer regions.

Optionally, a selectable marker may be associated with the nucleic acid sequence to be inserted. As used herein, the term "marker" refers to a gene encoding a trait or a phenotype which permits the selection of, or the screening for, a plant or plant cell containing the marker. The marker gene may be an antibiotic resistance gene whereby the appropriate antibiotic can be used to select for transformed cells from among cells that are not transformed. Examples of suitable selectable markers include adenosine deaminase, dihydrofolate reductase, hygromycin-B-phospho-transferase, thymidine kinase, xanthine-guanine phospho-ribosyltransferase and amino-glycoside 3'-O-phospho-transferase II (kanamycin, neomycin and G418 resistance). Other suitable markers will be known to those of skill in the art.

Vector(s) employed in the present invention for transformation of a plant cell include a nucleic acid sequence encoding DAS5, operably associated with a promoter. To commence a transformation process in accordance with the present invention, it is first necessary to construct a suitable vector and properly introduce it into the plant cell. Details of the construction of vectors utilized herein are known to those skilled in the art of plant genetic engineering.

DAS5 nucleic acid sequences utilized in the present invention can be introduced into plant cells using Ti plasmids of *Agrobacterium tumefaciens*, root-inducing (Ri) plasmids, and plant virus vectors. (For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9, and Horsch, et al., *Science,* 227:1229, 1985, both incorporated herein by reference). In addition to plant transformation vectors derived from the Ti or root-inducing (Ri) plasmids of Agrobacterium, alternative methods may involve, for example, the use of liposomes, electroporation, chemicals that increase free DNA uptake, transformation using viruses or pollen and the use of microprojection.

One of skill in the art will be able to select an appropriate vector for introducing the DAS5-encoding nucleic acid sequence in a relatively intact state. Thus, any vector which will produce a plant carrying the introduced DNA sequence should be sufficient. Even use of a naked piece of DNA would be expected to confer the properties of this invention, though at low efficiency. The selection of the vector, or whether to use a vector, is typically guided by the method of transformation selected.

Transformation of plants in accordance with the invention may be carried out in essentially any of the various ways known to those skilled in the art of plant molecular biology. (See, for example, *Methods of Enzymology, Vol.* 153, 1987, Wu and Grossman, eds., Academic Press, incorporated herein by reference). As used herein, the term "transformation" means alteration of the genotype of a host plant by the introduction of DAS5 nucleic acid sequence.

For example, a DAS5 nucleic acid sequence can be introduced into a plant cell utilizing *Agrobacterium tumefaciens* containing the Ti plasmid, as mentioned briefly above. In using an *A. tumefaciens* culture as a transformation vehicle, it is most advantageous to use a non-oncogenic strain of Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology,* 1:262, 1983; Hoekema, et al., *Nature,* 303:179, 1983).

Methods involving the use of Agrobacterium in transformation according to the present invention include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in planta transformation by Agrobacterium, as described by Bechtold, et al., (*C. R. Acad. Sci. Paris,* 316:1194, 1993) and exemplified in the Examples herein. This approach is based on the vacuum infiltration of a suspension of Agrobacterium cells.

The preferred method of introducing DAS5-encoding nucleic acid into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, DAS5 encoding nucleic acid sequences according to the present invention can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

DAS5 nucleic acid sequences can also be introduced into plant cells by electroporation (Fromm, et al., *Proc. Natl. Acad. Sci., U.S.A.,* 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing DAS5 nucleic acid into a plant cell is by means of high velocity ballistic penetration by small particles with the nucleic acid to be introduced contained either within the matrix of such particles, or on the surface thereof (Klein, et al., *Nature* 327:70, 1987). Bombardment transformation methods are also described in Sanford, et al. (*Techniques* 3:3, 1991) and Klein, et al. (*Bio/Techniques* 10:286, 1992). Although typically, only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing DAS5 into the plant cell, including chemical and physical means as described above. Preferably, contacting refers to introducing the nucleic acid or vector into plant cells (including an explant, a meristem or a seed), via *Agrobacterium tumefaciens* transformed with the DAS5 encoding nucleic acid as described above.

Plant Regeneration

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration (see *Methods in Enzymology,* Vol. 118, and Klee, et al., *Annu. Rev. Plant Physiol.,* 38:467, 1987). Utilizing the leaf disk-transformation-regeneration method of Horsch, et al. (*Science,* 227:1229, 1985), disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The resulting inbred plant produces seed containing the newly introduced foreign gene(s). These seeds can be grown to produce plants that would produce the selected phenotype, e.g. increased yield.

Parts obtained from one or more regenerated plants, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences. Plants exhibiting increased yield or biomass as compared with wild-type plants can be selected by visual observation. The invention includes plants produced by the method of the invention, as well as plant tissue and seeds.

In another embodiment, the invention provides for a method for producing genetically modified plants with increased levels of various brassinosteroids. Several genes have been found to encode proteins involved in brassinosteroid biosynthetic pathways. For example, DAS1, also known as DWF4, is thought to act between 5-α-campestanol and 6-deoxycathasterone of the late C-6 oxidation branch of the pathway, or, in the early C-6 oxidation branch, between 6-oxocampestanol and cathasterone. The DET2 protein also acts on the brassinosteroid pathway, upstream of DWF4 (DAS1) action (from (24R) 24-Methyl-cholest-4-en-3-one to (24R) 24-Methyl-cholest-5α-en-3-one).

The effect of high levels of the DAS5 protein or the DAS1 protein on levels of the various brassinosteroid intermediates was determined. Activation-tagged das5 (das5-D) and activation tagged das1 (das1-D) were transformed to either wild-type Arabidopsis plants, or to Arabidopsis plants carrying the det2 mutation. The Arabidopsis seedlings were grown under short day conditions (8 hours light, 18 hours dark) for 5 weeks. Rosette leaves were then harvested, flash frozen, and subjected to GC-MS analysis. Results are listed in Table 1, below. High levels of DAS5 result in increased levels of several of the brassinosteroid intermediates. Additionally, the effects of activation-tagged das1-D or activation-tagged das5-D in the presence of the det2 mutation was also determined. The presence of das5-D in the det2 mutant background resulted in increased levels of some of the brassinosteroids as compared to levels in the det2 mutant plants.

promoter, to obtain a transformed plant cell; producing a plant from the transformed plant cell; and thereafter selecting a plant exhibiting increased yield.

In another embodiment, the invention provides a method for producing a genetically modified plant characterized as having increased fresh weight as compared to a plant which has not been genetically modified (e.g., a wild-type plant). As used herein, the term "fresh weight" refers to the weight of a whole plant, plant part, plant tissue, or plant cells upon harvesting and debris removal, before significant dehydration-related water loss has occurred. The method includes the steps of contacting a plant cell with at least one vector containing at least one nucleic acid sequence encoding DAS5, wherein the nucleic acid sequence is operably associated with a promoter, to obtain a transformed plant cell; producing a plant from the transformed plant cell; and thereafter selecting a plant exhibiting increased fresh weight.

In another embodiment, the invention provides a method for producing a genetically modified plant characterized as having increased dry weight as compared to a plant which has not been genetically modified (e.g., a wild-type plant). As used herein, the term "dry weight" refers the weight of a whole plant, plant part, plant tissue, or plant cells after debris removal and subsequent drying in a low temperature

TABLE 1

| Compound | WT | det2 | das1-D/det2 | das1-D/WT | das5-D/det2 | Das5-D/WT |
|---|---|---|---|---|---|---|
| 24-methylene-cholesterol | 1880 | 480 | 480 | 2340 | 360 | 1400 |
| campesterol | 30000 | 9900 | 9400 | 13300 | 9900 | 24900 |
| campestanol | 490 | 3 | 4 | 590 | 11 | 420 |
| 6-oxocampestanol | 59 | 24 | 17 | 24 | 16 | 33 |
| 6-deoxocathasterone | 0.79 | 0.23 | 0.08 | 21.1 | 0.95 | 32.0 |
| 6-deoxoteasterone | 0.23 | 0.28 | 0.20 | 0.57 | 0.64 | 1.00 |
| 6-deoxotyphasterol | 1.59 | 0.07 | 0.10 | 4.61 | 0.15 | 8.43 |
| 6-deoxocastasterone | 2.31 | 0.01 | 0.06 | 11.2 | 0.09 | 15.2 |
| cathasterone | nd | nd | 0.23 | Nd | 0.59 | 0.15 |
| teasterone | nd | nd | nd | Nd | nd | nd |
| typhasterol | 0.03 | 0.39 | 0.53 | 0.03 | 0.80 | 0.19 |
| castasterone | 0.24 | 0.04 | 0.11 | 0.14 | 0.17 | 0.57 |
| brassinolide | nd | nd | nd | Nd | nd | nd | content (ng/g fw), nd: not detected (below detection limit)

In yet another embodiment, the invention provides a method for producing a genetically modified plant cell such that a plant regenerated from said cell produces increased yield as compared with a wild-type plant. The method includes contacting the plant cell with a DAS5 nucleic acid sequence to obtain a transformed plant cell; growing the transformed plant cell under conditions suitable for regeneration, and obtaining a plant having increased yield. Progeny may be derived by asexual propagation, apomictic reproduction, or sexual reproduction of the regenerated plant containing a DAS5 nucleic acid. Conditions such as environmental and promoter-inducing conditions vary from species to species, and optional conditions can be determined by one of ordinary skill in the art.

In another embodiment, the invention provides a method for producing a genetically modified plant characterized as having increased yield as compared to a plant which has not been genetically modified (e.g., a wild-type plant). The term "yield" has been previously defined herein. The method includes the steps of contacting a plant cell with at least one vector containing at least one nucleic acid sequence encoding a DAS5 polypeptide of the present invention, wherein the nucleic acid sequence is operably associated with a oven (for example, 70° C. for 48 hours) to remove excess $H_2O$. The method includes the steps of contacting a plant cell with at least one vector containing at least one nucleic acid sequence encoding DAS5, wherein the nucleic acid sequence is operably associated with a promoter, to obtain a transformed plant cell; producing a plant from the transformed plant cell; and thereafter selecting a plant exhibiting increased dry weight.

Table 2 below summarizes the results of fresh weight and dry weight measurements of Arabidopsis plants transformed with the das5-D construct. Measurements were calculated as a percentage of the wild-type control measurements. Interestingly, both fresh weight and dry weight increased by approximately 26% over the control plants.

TABLE 2

| Plant | Fresh Weight | Dry Weight |
|---|---|---|
| WT | 100% | 100% |
| Das5 | 126% | 126% |

Of particular agronomic importance is the finding that plants expressing high amounts of the DAS5 protein also have higher fresh weight and dry weight than control plants containing normal levels of the DAS5 protein. For example, when the activation tagged das5 gene (das5-D) introduced and expressed in Arabidopsis, the resulting mature plants had a 26% increase in fresh weight, and a 26% increase in dry weight. This may be of importance to the agricultural industry, as transformation with the das5-D gene may result in higher yields in many different types of crops. For example, increased yields of alfalfa, lettuce, corn, wheat, barley, or rice may be increased when transformed with the activation-tagged das5. Tree crops such as apple, pear, plum, avocado, mango, papaya, etc. may have higher yields, and trees used for the timber industry may be able to produce more lumber.

The activation-tagged das5 gene may be operably linked to tissue-specific promoters to increase the specificity of the increased yield that occurs when das5 is expressed at high levels. This tissue-specificity may be tailored to specific crops so that the biomass of desired tissues is increased, but unusable tissues do not increase in biomass. For example, fruit trees may be transformed with the activation-tagged das5 gene linked to fruit-specific promoters, so that the gene is expressed more highly in fruit tissues. This may result in larger fruit. As another example, carrots or turnips may be transformed with the DAS5 gene linked to root-tissue specific promoters so that most of the biomass increase is in the useable root tissue. Further, the activation-tagged DAS5 gene may be linked to seed-specific promoters to increase yield in seeds. This may be particularly useful in corn, barley, rice, wheat, or other cereal crops. It may also be useful to produce higher levels of seed tissue in oil crops such as palm oil, coconut oil, or safflower oil. Larger nuts such as peanut, hazelnuts, macadamia nuts, or sunflower seeds may result from overexpression of the das5 gene coupled with seed-specific promoters.

The DAS5 gene or activation-tagged das5 gene (das5-D) may also be operably linked to environmentally inducible promoters to produce crops with desirable agricultural characteristics. For example, the activation-tagged das5 gene could be linked to both cold-specific promoters and seed specific promoters so that when cold weather begins, DAS5 is highly expressed in the seed, signaling more of the crop's biomass to accumulate in the seed rather than in unusable leaf material which will die when colder weather arrives. In contrast, the activation-tagged das5-D construct could be linked to root-specific promoters and drought-specific promoters such that, upon water stress, growth is focused toward more root growth to increase water uptake. This may result in increased survival under poor environmental conditions.

Crops containing a high level of the DAS5 protein may also require larger nutrient inputs or increased water. Therefore, in some cases it may be useful to link the das5-D construct to heterologous promoters such that the DAS5 protein is highly expressed when abundant water and nutrients are available, but is downregulated under water or nutrient stress. This would potentially increase the plasticity of the system by making plants more resistant to natural changes in weather cycles or to changes in fertilizer application strategies.

In another embodiment, the invention provides a method of producing a plant characterized as having increased yield by contacting a susceptible plant with a DAS5 promoter-inducing amount of an agent which induces DAS5 gene expression, wherein induction of DAS5 gene expression results in production of a plant having increased yield as compared to a plant not contacted with the agent.

A "susceptible plant" refers to a plant that can be induced to utilize its endogenous DAS5 gene to achieve increased yield. The term "promoter inducing amount" refers to that amount of an agent necessary to elevate DAS5 gene expression above the level of DAS5 expression in a plant cell not contacted with the agent. For example, a transcription factor or a chemical agent may be used to elevate gene expression driven by a DAS5 native promoter, thereby inducing promoter activity and DAS5 gene expression.

In another aspect of the invention, it is envisioned that increased expression of DAS5 in a plant cell or in a plant, increases resistance of that cell/plant to plant pests or plant pathogens. For example, field studies have shown that brassinolides are effective as pesticides, therefore, increased expression of DAS5 would result in increased amounts of brassinolide in the plant. In addition, increased DAS5 expression may also act as a herbicide safener by increasing the plant's resistance to pesticides. By the term "safener" is meant a gene that responds to specific chemicals (such as a pesticide) by activating natural plant pathways. The DAS5 protein may therefore protect plants against pests as well as against pesticides.

The above disclosure generally describes the present invention. A more complete understanding can be obtained by reference to the following specific examples which are provided herein for purposes of illustration only and are not intended to limit the scope of the invention.

EXAMPLE 1

Generation of Arabidopsis Mutations Using an Activation Tagging Approach

The dominant mutation das5-D was isolated from a set of several thousand Arabidopsis plants transformed with the activation-tagging vectors following the method of Weigel, et al., (*Plant Physiol.* 122:1003, 2000), with modifications described below. Activation tagging utilizes T-DNA vectors that contain multimerized transcriptional enhancers from the cauliflower mosaic virus (CaMV) 35S gene. In this method, the activation tagging sequence serves to upregulate endogenous genes that are downstream of the insertion site. In fact, overexpressed genes are almost always found immediately adjacent to the inserted CaMV 35S enhancers, at distances ranging from 380 bp to 3.6 kb. The activation-tagging vectors additionally contain selectable marker genes. The T-DNA vector was modified from the method of Weigel (supra) by the addition of a transposable element, so that, if desired, loss-of-function alleles of the tagged mutant may be created by activating the transposon.

The activation tagged sequences were introduced into Arabidopsis using Agrobacterium-mediated transformation. Arabidopsis plants were grown at 23° C. in long-day conditions (16 h of light and 8 h of dark) under a mixture of 3:1 cool-white:Gro-Lux fluorescent lights (Osram Sylvania, Danvers, Mass.). The activation tagging vector pSK1015, conferring glufosinate resistance (Weigel, et al, (2000), supra) was introduced into *Agrobacterium tumefaciens*. *Arabidopsis thaliana* plants of the det 2 mutant background (originally derived from the Columbia wild-type strain Col-0) were transformed by dipping the flower buds into a solution of Agrobacterium containing the activation-tagging vectors. Seeds from the Agrobacterium-treated plants were mixed with 0.1% (w/v) Phytagar (Gibco, Rockville, Md.), incubated at 4° C. for 2 d for stratification, and sown directly on soil (pools of Columbia wild-type strain Col-7 seeds transformed with activation-tagging vector pSK1015 conferring glufosinate resistance are now publicly available from the Arabidopsis Biological Resource Center (Ohio State University, Columbus). Plants were grown under a 16 hour light /8 hour dark cycle. A 6% solution of the herbicide ammonium glufosinate was diluted 1:1,000 in H2O and sprayed on the plants twice a week for three weeks to select for transformed plants.

Primary transformants generated by vacuum infiltration of *Agrobacterium tumefaciens* and hemizygous for T-DNA insertions. Therefore, plants could be screened after selection for herbicide resistance, since dominant mutations, as expected for activation tagging, will be already apparent in the hemizygous state. Primary transformants were therefore screened directly for an overall larger size as compared to control plants. The das5-D mutant was selected for further examination due to its altered phenotypic characteristics: larger rosette leaves, longer petioles, and taller peduncles.

EXAMPLE 2

Identification of the DAS5 Gene Using Plasmid Rescue

Activation-tagged regions of plant genomic DNA were isolated by a plasmid rescue technique. For plasmid rescue, genomic DNA was prepared from 0.1 g of plant tissue using a DNA extraction kit (Phytopure, Nucleon Biosciences, Glasgow, UK). The extracted DNA was resuspended in 100 µL of TE buffer (10 mM Tris-HCl, pH 8.0; 1 mM EDTA, pH 8.0), and purified twice by phenol-chloroform extraction. The plasmid sequences in pSKI015 are flanked by several restriction enzyme sites that can be used for rescue of T-DNA and adjacent plant sequences from transformed plants. For example, the restriction enzymes KpnI, EcoRI, and HindIII, and PstI can be used for rescue of sequences adjacent to the right T-DNA border, and BamHI, SpeI, and NotI can be used for sequences adjacent to the left border. 10 µL of genomic DNA was digested overnight with the appropriate restriction enzyme in a 100-µL reaction. Samples were ligated overnight at 14° C. in a total volume of 250 µL. Ligated DNA was precipitated and transformed by electroporation into recombination-deficient *E. coli* SURE cells (Stratagene), to maximize stability of the multimerized CaMV 35S enhancers. The plant genomic DNA in a KpnI rescued plasmid was sequenced using the ABI370 automated sequencer.

EXAMPLE 3

Sequence Comparison of DAS5 with other Cytochrome p450 Proteins

BLAST (Basic Local Alignment Search Tool) is a computer-automated amino acid sequence and nucleic acid sequence comparison and identification tool. The heuristic search algorithm BLAST 2.2.1 (Altschul, et al., *Nucleic Acids Res.* 25:3389, 1997; Altschul, et al., *J. Mol. Biol.* 215:403, 1990; and Madden, et al., *Meth. Enzymol.* 266:131, 1996, incorporated herein by reference) was used to search for proteins similar to the DAS5 protein sequence. The BLASTP tool (available at ncbi.nih.gov/BLAST) takes protein sequences in FASTA format, GenBank Accession numbers or GI numbers and compares them against the NCBI protein databases.) The DAS5 sequence was queried against the non-redundant database using the standard protein-protein BLASTP version 2.2.1 (Apr. 13, 2001) with the following settings: matrix=BLOSUM62, gap costs: Existence: 11, Extension: 1. The % identity and % similarity (positives) measurements were determined by a pairwise blast search "BLAST 2 sequences" results version BLASTP" (Tatusova, et al., FEMS *Microbiol Lett.* 174:247, 1999, incorporated herein by reference).

EXAMPLE 4

Production of Transgenic Arabidopsis Plants Containing the DAS5 Sequence

To confirm that the overexpressed DAS5 gene caused the large plant phenotype, and to further determine if levels of brassinosteroids are altered in response to DAS5 overexpression, the rescued DAS5 genomic fragment, along with its upstream activation tag sequences, was transformed to Arabidopsis plants using Agrobacterium-mediated transformation. The sequence was ligated into a vector suitable for introduction into Agrobacterium, then plants were transformed by the method described in example 1.

EXAMPLE 5

Transgenic Arabidopsis Plants Containing Multiple Alterations in the Brassinosteroid Pathway To examine changes in brassinosteroid levels in response to overexpression of DAS5, with or without the presence of other proteins (such as DAS1, homolog to the DWF4 cytochrome p450, which is also part of the brassinosteroid pathway), activation tagged das5 (das5-D) and activation tagged das1 (das1-D) were transformed to either wild-type Arabidopsis plants, or to Arabidopsis plants carrying the det2 mutation. The det2 lesion is also in the brassinosteroid pathway, upstream of DWF4 (DAS1) action (from (24R) 24-Methyl-cholest-4-en-3-one to (24R) 24-Methyl-cholest-5α-en-3-one). Plants were grown under short day conditions (8 hours light, 18 hours dark) for 5 weeks. Plant material was harvested and flash frozen in liquid nitrogen. The plant material was then lyophylized and ground to a fine powder using a mortar and pestle prior to analysis for brassinosteroid content.

EXAMPLE 6

Measurement of Brassinsteroid Levels Produced in Transgenic Plants Carrying the Das5-D Gene To quantify levels of the various brassinosteroid pathway intermediates, plant tissue samples were prepared as described above and analyzed by HPLC purification, subsequent derivatization, and gas chromatography-selected ion analysis following the method of Noguchi et al., *Plant Physiol.* 122:743–752, 1999. Briefly, the lyophilized plant material (50 g fresh weight equivalent) was extracted two times with 500 mL of MeOH, and deuterium-labeled internal standards (1 ng/g fresh weight) were added.

In preparation of HPLC separation, the MeOH extract was loaded onto a silica gel cartridge (Sep-Pak Vac, Waters, Milford, Mass.), and eluted with 30 ml of chloroform, followed by 3% MeOH in chloroform, followed by 20% MeOH in chloroform. After subsequent purification with an ODS cartridge (Sep-Pak Plus C18, Waters, Milford, Mass.), eluates were subjected to ODS-HPLC (Senshu Pak Pegasil ODS, 10×30 mm+Senshu Pak Pegasil ODS, 20×250 mm; Senshu Scientific, Tokyo) at a flow rate of 8 mL/ minute, all according to the method of Noguchi et al. (supra).

The HPLC fractions were then derivatized in preparation for GC-SIM analysis. Fractions containing brassinolide, castasterone, and 6-deoxocastasterone were derivatized to bis-methaneboronate, while fractions of teasterone, typhasterol, 6-deoxoteasterone, and 6-deoxotyphasterol were derivatized to methaneboronate-trimethylsilyl ether. GC-MS analysis was performed using a mass spectrometer (Automass JMS-AM150, JEOL, Tokyo) connected to a gas chromatograph (model 5890A-II, Hewlett-Packard, Wilmington, Del.) with electron ionization (70 eV) with a source temperature of 210° C., and a DB-5 column (J&W Scientific, Folsom, Calif.; 15-m×0.25-mm, 0.25-μm film thickness). The injection temperature was set at 250° C. The column temperature program was set at: 80° C. for 1 min, raised to 320° C. at a rate of 30° C./minute, then 5 minutes at 320° C. The interface temperature was 250° C. and the carrier gas was He at a flow rate of 1 mL/min with splitless injection. The endogenous levels of brassinosteroids were determined as the ratio of the peak area of molecular ions for the internal standard to that of the endogenous brassinosteriod.

EXAMPLE 7

Transgenic das5-D Arabidopsis Plants have Increased Fresh Weight and Dry Weight

Arabidopsis plants containing the activation tagged-das5-D gene were grown side by side with wild type Arabidopsis control plants under a 16 hour light/9 hour dark cycle. After 5 weeks, plants were harvested and washed to remove excess debris. The fresh weight of each plant was measured. To determine dry weight, the plants were then placed on metal weigh dishes which were dried in an oven at 70° C. for 48 hours. The dry weight measurement, calculated as a percentage of the control plant dry weight measurement, is displayed in Table 2.

What is claimed is:

1. A method of producing a genetically modified plant having increased plant growth or increased plant biomass as compared to a wild-type plant, comprising:
transforming a plant cell with at least one nucleic acid encoding a polypeptide having at least 95% sequence identity with SEQ ID NO:1, said nucleic acid being operably associated with a promoter, to obtain a transformed plant cell;
producing a plant from said transformed plant cell;
allowing said nucleic acid to be expressed; and
selecting a plant exhibiting said increased plant growth or increased plant biomass.

2. The method of claim 1, wherein the transformation is by physical means.

3. The method of claim 1, wherein the transformation is by chemical means.

4. The method of claim 1, wherein the promoter is selected from the group consisting of a constitutive promoter and an inducible promoter.

5. The method of claim 1, wherein said polypeptide has the amino acid sequence of SEQ ID NO: 1.

6. The method of claim 1, wherein said nucleic acid has the sequence of SEQ ID NO: 3.

7. A genetically modified plant exhibiting increased plant growth or increased plant biomass in comparison to a wild-type plant, wherein said genetically modified plant comprises at least one exogenous nucleic acid, wherein said nucleic acid encodes an amino acid sequence with at least 95% sequence identity with the amino acid sequence shown in SEQ ID NO:1.

8. The genetically modified plant of claim 7, wherein the exogenous nucleic acid is operably linked to a promoter selected from the group consisting of: a constitutive promoter and an inducible promoter.

9. The genetically modified plant of claim 7, wherein said amino acid has the amino acid sequence of SEQ ID NO: 1.

10. The genetically modified plant of claim 7, wherein said exogenous nucleic acid comprises the sequence of SEQ ID NO: 3.

11. The genetically modified plant of claim 7, wherein the plant is a dicotyledonous plant.

12. The genetically modified plant of claim 7, wherein the plant is a monocotyledonous plant.

13. A genetically modified seed, wherein said seed produces a plant exhibiting increased plant growth or increased plant biomass in comparison to a wild-type plant, wherein said genetically modified seed comprises at least one exogenous nucleic acid encoding a DAS5 polypeptide, wherein said polypeptide comprises an amino acid sequence with at least 95% sequence identity with SEQ ID NO:1.

14. The genetically modified seed of claim 13, wherein the exogenous nucleic acid is operably linked to a promoter selected from the group consisting of: a constitutive promoter and an inducible promoter.

15. The genetically modified seed of claim 13, wherein said amino acid has the amino acid sequence of SEQ ID NO: 1.

16. The genetically modified seed of claim 13, wherein said exogenous nucleic acid has at least 95% sequence identity with the sequence of SEQ ID NO: 3.

17. An isolated DAS5 polynucleotide encoding the amino acid sequence of SEQ ID NO:1.

18. The DAS5 polynucleotide of claim 17, wherein the polynucleotide has the sequence of SEQ ID NO: 3.

* * * * *

SEQUENCE LISTING

```
<160> NUMBER OF SEQ ID NOS: 3

<210> SEQ ID NO 1
<211> LENGTH: 382
<212> TYPE: PRT
<213> ORGANISM: DAS5

<400> SEQUENCE: 1

Met Gly Trp Pro Phe Ile Gly Glu Thr Ile Ser Phe Phe Lys Pro His
 1               5                  10                  15

Arg Ser Asp Ser Ile Gly Thr Phe Leu Gln Gln Arg Val Ser Arg Tyr
            20                  25                  30

Gly Lys Val Phe Lys Ser Asn Ile Cys Gly Gly Lys Ala Val Val Ser
        35                  40                  45

Cys Asp Gln Glu Leu Asn Met Phe Ile Leu Gln Asn Glu Gly Lys Leu
    50                  55                  60

Phe Thr Ser Asp Tyr Pro Lys Ala Met His Asp Ile Leu Gly Lys Tyr
65                  70                  75                  80

Ser Leu Leu Leu Ala Thr Gly Glu Ile His Arg Lys Leu Lys Asn Val
                85                  90                  95

Ile Ile Ser Phe Ile Asn Leu Thr Lys Ser Lys Pro Asp Phe Leu His
            100                 105                 110

Cys Ala Glu Asn Leu Ser Ile Ser Ile Leu Lys Ser Trp Lys Asn Cys
        115                 120                 125

Arg Glu Val Glu Phe His Lys Glu Val Lys Met Phe Thr Leu Ser Val
    130                 135                 140

Met Val Asn Gln Leu Leu Ser Ile Lys Pro Glu Asp Pro Ala Arg Leu
145                 150                 155                 160

Tyr Val Leu Gln Asp Phe Leu Ser Tyr Met Lys Gly Phe Ile Ser Leu
                165                 170                 175

Pro Ile Pro Leu Pro Gly Thr Gly Tyr Thr Asn Ala Ile Lys Val Arg
            180                 185                 190

Ser Asn Arg Asn Ile His Gln Asn Ala Ile Ile Glu Asp Met Asn Asn
        195                 200                 205

Ala Ile Arg Glu Glu Asp Phe Leu Asp Ser Ile Ile Ser Asn Glu Asp
    210                 215                 220

Glu Glu His Ala Ala Ile Arg Ala Lys Lys Gly Asp Gly Glu Leu Leu
225                 230                 235                 240
```

```
Asn Trp Glu Asp Tyr Gln Lys Met Glu Phe Thr Gln Cys Val Ile Ser
                245                 250                 255
Glu Ala Leu Arg Cys Gly Asn Ile Val Lys Thr Val His Arg Lys Ala
            260                 265                 270
Thr His Asp Ile Lys Phe Lys Glu Tyr Val Ile Pro Lys Gly Trp Lys
        275                 280                 285
Val Phe Pro Ile Phe Thr Ala Val His Leu Asp Pro Ser Leu His Glu
    290                 295                 300
Asn Pro Phe Glu Phe Asn Pro Met Arg Trp Thr Lys Thr Thr Ala Phe
305                 310                 315                 320
Gly Gly Gly Val Arg Val Cys Pro Gly Gly Glu Leu Gly Lys Leu Gln
                325                 330                 335
Ile Ala Phe Phe Leu His His Leu Val Leu Ser Tyr Arg Trp Lys Ile
                340                 345                 350
Lys Ser Asp Glu Met Pro Ile Ala His Pro Tyr Val Glu Phe Lys Arg
            355                 360                 365
Gly Met Leu Leu Glu Ile Glu Pro Thr Lys Phe Leu Glu Asp
        370                 375                 380

<210> SEQ ID NO 2
<211> LENGTH: 6508
<212> TYPE: DNA
<213> ORGANISM: DAS5

<400> SEQUENCE: 2
catctccatt ggtgagatac ttcatgagta cttcataata tattattaat atttttatgt    60
ttaatttaag tagaaaaatt tatactaaaa ttgtatttcc attggtatga gtatctcatt   120
aacattaaca tattattata tgttttttat attaaattta atatatctac aatattttca   180
aacatatcaa ttatttattt ttacaaatta tattattaaa tagttttatt attttttaaa   240
ccataattaa acataattaa acattacttt acatataaaa tcataataaa aaatttataa   300
attaaatata aaattacata taaaaccatg ataacataaa ttaaatagaa aaaatatata   360
aattaaaccg aaattacata taaaaccatg ataacataaa tcaaagctaa ctatattatc   420
tattatggtt ttactcttca tttgatgatg caccaaactt ttgtcatata tgctcaacta   480
ggtcatcttt tagttgttgg tgcatatctc tatcacgaag tcgaattcga ttgccgagaa   540
tgttgcaaaa taaaaataga aaattttttaa gttattatta tgtttaatgc ttaactaaca   600
ccaattaaat aatattcgta tataatttaa acatatacat gatgagagct tattatatag   660
ataatttaat tttatgaatt ttaaaagtaa aaataaaaaa aataacaaac atataaagta   720
tttaattgat gttataaagt atagataatt ttatttataa caaagaaaag aaattaataa   780
caaggtgaca tatggaagag agagaaagtt tctccaagtt tctcatttca gaacgattc    840 tgagaaaaac tgattaaaaa attattattt tcatattttt gatttatttt tatttggagt   900
ttctcagtga gaaactaccg atggagatgg tcttacttgc ttacttcaac aaaaaaaaat   960
cttaatatat ataataatt tatgtctgtt gagtacatca tcacatatct ataatcaaac  1020
gattatatag gattttaatt agctgttatt tttgtgaata gcatgcgatc aagtgaatga  1080
aaagcgaatt atagatgaaa acaacaacga atgtaaataa aagtcaaaag ataacgaaaa  1140
gtgtcattta cgaagataga gagtttactt tgaaagaaca taaatttata ccaacaaact  1200
tattgcatga gggtcccaaa ttgcgtacac gtgcgtcaat ttttcatcat ttagtttctt  1260
acattcctct tttgacaaaa aaaataaaag tttcttacat tcctcttata tacttttttg  1320
```

```
ttcttctgcg atctgcattc tcaattattt tgtctgattg actcgataaa tttacgaggt    1380
tctcttaaaa aaatgtttac acgaagtatt tagattttcc tttgttattt tactagctag    1440
ttaaccatga atcatttga gaggacaaga atatatataa aacattattt tattctcagt    1500
atcaaaaaaa aaaatttatt gttttcataa tttcaatttt tttttttatg tgttctagtt    1560
tttgttaaca ctatttttcc caatgaaaac tattattaaa taacaatgtt ttgggattgt    1620
acataaataa taataataat aataataata ataataataa taataataat aataataata    1680
ataaaaataa taatgttttg cataccgccg ttttaccatt ttgattgtca attctaaata    1740
tattgttatc ttttatagtt atttttttatt attaaaaaaa tgtgtactgt ttatgtcaat    1800
agtagaatta gacaaagtat gtgcaatctt tttcgcaata ttcctatttt attagcaaac    1860
ggtaaaaaaa ataaaataaa aacaagtaaa acatttgtca tagtctagtt attaattata    1920
gtgaaatcat atgattatgt aataatcatg tttttaaata ctaataagac tatatggata    1980
tcataagcag atacaagttt tagcttgtta tatacatgct taattaatta ttttttcata    2040
tcttaagata atttgaaata gcttatatat gatattgtta aatttaatat ctaatccaat    2100
agtactggat tttaattat atatatatat atatattttt aaataattat taaacattaa     2160
taattagata tgttaaattc tagaagaata aattacatgt tatcatattg ggagaatagt    2220
catatttcca ttgttatcac tgatttgatt ccaagtgtgt agtatgagag atttctgtag    2280
gatgcaacaa tatactttct tttttatttac actaaaatat tatctaaatc aacaataaga    2340
atgattatat aaagattatt ttttctgtta tacataagaa aagagttgtt ggtttctctt    2400
ttttgtctct acacaattag gaatgttccc ctatagtata gtatatattt tactttcgtg    2460
gatcttctta gatatactac ctttaatttg gttgtttgtg agtgtgagtg ttagtgtaag    2520
tgtggtgtgg ttgtgtatg tgtatgtgta tatatatata tatatagaga gagaggtata    2580
tagatagacc aagaagaaaa catcataata gatactcaat tatcaataaa aggatcttaa    2640
tctaattcaa agacaatgct ggtcttatcc atcttcttgt cgttaggatt gttctttctc    2700
tctattttga ttcttatat ttcaatttct aagaaaaatg aaacaaacga tcatcactca    2760
tcactaactg gcagcatggg atggcctttc attggagaaa ctatttcttt cttcaaacct    2820
catagatcag actccatcgg tacattcttg caacaacgtg tttcacggta ataattaaca    2880
tgttcttttt atttcttttg ttgttgttgt caattgtagt gcgaaattta aattgtgtag    2940
ttagcaacaa caaaaaaact gtgtagacaa caatatacac ccttcatggg aactcagttt    3000
tcaaaaatca attgaaccaa attggctttc agcaaaaaac gtattagcca cttaatgcct    3060
aaacaccaaa taacctatt tctttaaagg atcattatat ttttatatat aattaattaa    3120
aagaaaaaag taatgttcac agtactacag aagattcata tctgattttt ttgcatacat    3180 gacaaatttga ttgcctacca atgttttatt gatttttatttt tgtaaatcca atttatatac  3240
tatacaacat ataatatatc tttttttttt ttgtttaagc ctaaattgac aataactgtg    3300
aatgttgtta ttcaggtatg gaaaagtgtt caagtcaaat atatgtggtg gaaaagcagt    3360
agtctcatgt gaccaagaac tcaacatgtt catacttcaa aacgaaggga agttgtttac    3420
atcggattat ccaaaagcga tgcatgacat tctcggcaaa tattcccttc tattagccac    3480
cggagaaatt cacaggaaac taaaaaatgt tattattagc ttcatcaatc tcacaaagtc    3540
gaaacctgac tttcttcact gcgcagagaa cctctctatc tcgatactaa agtcatggaa    3600
aaattgccga gaagtcgaat tccataaaga agttaaaatg gtaattaatt aatcactgaa    3660
```

-continued

```
tccttataat caatattgtt ataattctga tatctttgtt gcggttgaat catacagttt    3720
actctcagtg ttatggtaaa ccaactcttg agcatcaagc cagaagaccc agcaagactt    3780
tatgtattgc aagattttt atcttatatg aaagggttta tctccttacc aataccgctt    3840
ccaggaacgg gttatacaaa cgcaattaag gttagatcca atcgtaatat acatcaaaac    3900
gcaattatag gttttgtttt cgtcgtttta tcaaaaaca ttaagccact aatttataag    3960
aaaataaaca attggattct aggttttgc agttcttgta tataacttgg gtcatgatga    4020
tgctttatca tatggttttc atgtaaacac atttatctgt atgtaaatac ataacatata    4080
tacacttaaa actatatagt tttaaagtca ttttcgatgt ttgccaggct aggaagagat    4140
tgtcggcgag ggttatgggg atgataaaag aaagagagcg cgaagaagaa gacatgaata    4200
atgcaataag agaagaagat tttctggatt cgataatttc gaatgaagat ctaaattatg    4260
aagagaaagt tagcattgtg ttggacattt tgcttggagg ctttgagaca agtgctacta    4320
ctctttcctt agtcgtctat tttctagcaa aatctccaaa tcttcttcac aaactcaagg    4380
tattctctct ctcttctcat tatctatata tttgtgcatg tatacacata cgtatatatg    4440
ttaatctatg tgaacgtata caggaagaac atgcagccat tagagccaag aaaggggatg    4500
gggaactttt gaattgggaa gattatcaga agatggaatt cactcaatgt gtatgtttca    4560
taaacccatc ccatcatttt atttatttt tgctatttt ttcgcaaatt tgttttggta    4620
cgtagccaag ttttttttctg atcatatgtt gatactactt taaaatcata tagaacatgt    4680
tcacttatat catgaaattt actggacgga atttgcaggt gatttctgag gcactacgat    4740
gtggtaatat cgtcaagact gtacatagaa aagctactca tgatattaaa ttcaaaggtt    4800
aacaaaaatg tcaatcattt ttttttgat caaaaaatgt caatcaaatt ttactaatta    4860
atgtacaaat caaattagtg tttctctaat atgtttgagt tgcagaatat gtgattccaa    4920
aggggtggaa ggtgtttcca atcttcacag cagtacatct tgatccctct cttcatgaaa    4980
atccttttga atttaatccc atgagatgga ccgtaagtaa attatttaga aacagataac    5040
attcaaatgg gttttttttt tttttttttt tttttttttt tttggcaaaa ataacattca    5100
aatggtaagc aaagaaaaaa aacggaaata ttgtgaaact aattttggtt tttaaattaa    5160
ataggataag gctaagatga acaagaaaac gacggcgttt ggaggaggag taagggtatg    5220
tcctggtggt gaacttggca agctccaaat tgctttcttc cttcatcatc ttgtcctctc    5280
ctataggttt gtctaatcac tcactatggt tgactaattt taattagtga acactgcctt    5340
atccgacata atcatctatt atactttggt taaaattttg gttggtttga ttttaaatc    5400 gttttgtttt gttatttttc ttctcaagtt ctcatgtttc agttatttta tactgatgga    5460
tacatctatt tgaaaaaata tgtgttttat catgttttaa tgttcaatat agctaagaag    5520
tttatttata atggtaggtg gaaaataaag tcagatgaaa tgccaatcgc gcaccttac    5580 gtggagttta agagaggcat gcttttggag atagagccaa caaattcct tgaagattag    5640 ctgctttaat aaggaatcca tcttagatga aaatttaatt aataactatt aaaaatgtaa    5700
tgtctaataa tatgctccat tcccaaatat aaagtactct ctagtcatag agttttgtgt    5760
tagttaggtg ttggagtttt gaaataaaat gagtatttgc ctttggatat ggtatattta    5820
tgttttgttt ctagaaaaat tatctaaaat attactattt cgagttttta tatcatatcc    5880
gcgttcaaat atttaattag tgttactagg caatctaaca caatactttt aaaataactc    5940
aaatcatgtg tatactataa agtagttagt gtattcgacc acactaataa gactttaagt    6000
taaaacatgt gtgaacttaa ctactatcca ttccattata tcatatgaat attttctttt    6060
```

```
atttttttcg tgaaaaagtt acaaaccaga cacataaacc acatgtaatt agaaaaaata      6120
cagaaacata actatagtta atgtttatcc gtctttacat aagaactcta ggaagagata      6180
atctagaggg gaagttacca ttttggcctt gaaaagattt gtcgaagaca tacttagcgt      6240
taagagaaga aggattaact tgcatgaaaa ggtaattacc ggcaaagaga tcaccaaagt      6300
gtgattgact ctccttcaac ctcttcaata tttttaaaat tccagttttt accctattcg      6360 cttttcttcct cacaaatcct ctaagtcttc ggatcttaac tctaaccccta atcctcctcc    6420 ttcctcccaa tgacaccact ctcttgaacc tgtataacag aaaagaaaga tggttcatca      6480
tgaaagtctt cgataatatc aaaacact                                         6508

<210> SEQ ID NO 3
<211> LENGTH: 1149
<212> TYPE: DNA
<213> ORGANISM: DAS5

<400> SEQUENCE: 3
atgggatggc ctttcattgg agaaactatt tctttcttca aacctcatag atcagactcc        60
atcggtacat tcttgcaaca acgtgtttca cggtatggaa aagtgttcaa gtcaaatata       120
tgtggtggaa aagcagtagt ctcatgtgac caagaactca acatgttcat acttcaaaac       180
gaagggaagt tgtttacatc ggattatcca aaagcgatgc atgacattct cggcaaatat       240
tcccttctat tagccaccgg agaaattcac aggaaactaa aaaatgttat tattagcttc       300
atcaatctca caaagtcgaa acctgacttt cttcactgcg cagagaacct ctctatctcg       360
atactaaagt catggaaaaa ttgccgagaa gtcgaattcc ataagaagt taaaatgttt        420 actctcagtg ttatggtaaa ccaactcttg agcatcaagc cagaagaccc agcaagactt       480
tatgtattgc aagattttt atcttatatg aaagggttta tctccttacc aataccgctt       540
ccaggaacgg ttatacaaa cgcaattaag gttagatcca atcgtaatat acatcaaaac       600
gcaattatag aagacatgaa taatgcaata agagaagaag attttctgga ttcgataatt       660
tcgaatgaag atgaagaaca tgcagccatt agagccaaga aagggggatgg ggaacttttg      720 aattgggaag attatcagaa gatggaattc actcaatgtg tgatttctga ggcactacga      780
tgtggtaata tcgtcaagac tgtacataga aaagctactc atgatattaa attcaaagaa      840
tatgtgattc caaagggtg gaaggtgttt ccaatcttca cagcagtaca tcttgatccc       900
tctcttcatg aaaatccttt tgaatttaat cccatgagat ggaccaaaac gacggcgttt       960
ggaggaggag taagggtatg tcctggtggt gaacttggca agctccaaat tgctttcttc     1020
cttcatcatc ttgtcctctc ctataggtgg aaaataaagt cagatgaaat gccaatcgcg     1080 caccctttacg tggagtttaa gagaggcatg cttttggaga tagagccaac aaaattcctt     1140
gaagattag                                                              1149
```